United States Patent [19]  
Dessau

[11] Patent Number: 4,665,247  
[45] Date of Patent: May 12, 1987

[54] DIELS-ALDER CYCLIZATION OVER COPPER-CONTAINING ZSM-12

[75] Inventor: Ralph M. Dessau, Edison, N.J.

[73] Assignee: Mobil Oil Corporation, New York, N.Y.

[21] Appl. No.: 798,662

[22] Filed: Nov. 15, 1985

[51] Int. Cl.$^4$ ................................................ C07C 2/50
[52] U.S. Cl. .................................... 585/361; 570/186; 570/215; 585/366; 585/431; 585/510; 585/533
[58] Field of Search ............... 585/366, 365, 361, 430, 585/510, 533; 570/186, 215

[56] References Cited

U.S. PATENT DOCUMENTS

| 2,974,176 | 3/1961 | Warner et al. | 585/366 |
| 3,444,253 | 5/1969 | RelmHager et al. | 260/666 |
| 4,019,880 | 4/1977 | Rabo et al. | 55/68 |
| 4,384,153 | 5/1983 | Dessau | 585/366 |
| 4,396,787 | 8/1983 | Gluzek et al. | 585/366 |
| 4,413,154 | 11/1983 | Dessau | 585/366 |

FOREIGN PATENT DOCUMENTS

| 2548428 | 5/1976 | Fed. Rep. of Germany | 585/366 |
| 1138126 | 12/1968 | United Kingdom | 585/366 |
| 1554942 | 5/1976 | United Kingdom | 585/366 |

*Primary Examiner*—Asok Pal  
*Attorney, Agent, or Firm*—A. J. McKillop; M. G. Gilman; L. P. Hobbes

[57] ABSTRACT

The present invention provides a process which is adapted for cyclodimerization of 1,3-butadiene to 4-vinylcyclohexene-1 under Diels-Alder conditions in the presence of a copper-containing ZSM-12.

4 Claims, No Drawings

DIELS-ALDER CYCLIZATION OVER COPPER-CONTAINING ZSM-12

BACKGROUND OF THE INVENTION

This invention relates to a catalytic process for the cyclization of alkene compounds, as exemplified by the cyclodimerization of 1,3-butadiene to 4-vinylcyclohexene-1 utilizing a catalyst comprising a copper-containing crystalline silicate having the structure of ZSM-12.

DESCRIPTION OF THE PRIOR ART

U.S. Pat. No. 3,444,253 discloses and claims a process for the dimerization of 1,3-butadiene to produce 4-vinylcyclohexene-1 using large pore copper (I) zeolite X, or copper (I) zeolite Y. Moreover, U.S. Pat. No. 4,384,153, incorporated herein by reference, discloses that large pore zeolites such as zeolite Y, zeolite beta and ZSM-20 in low acidity form, e.g., alkali metal-exchanged zeolites, are useful for such dimerization while low acidity zeolites of smaller pore size such as ZSM-5 and ZSM-12 are not. U.S. Pat. No. 4,413,154, incorporated herein by reference, teaches the cyclization of alkene compounds with a large-pore carbon molecular sieve. Copper-containing zeolites have been disclosed in U.S. Pat. No. 4,019,880, incorporated herein by reference, as being useful in the sorption of carbon monoxide.

The present invention represents an effective alternative to the prior art techniques in that it has been found that a high Diels-Alder conversion can be obtained from an intermediate pore size copper-containing zeolite by utilizing copper-comtaining ZSM-12 as the intermediate pore size zeolite.

DESCRIPTION OF THE PREFERRED EMBODIMENTS

It is to be noted that the intermediate pore size crystalline metallosilicates with which this invention is concerned are well known in the art. Zeolite ZSM-12 is disclosed and claimed in U.S. Pat. No. 3,832,149, incorporated herein by reference.

An important characteristic of the crystal structure of ZSM-12 is that it provides a selective constrained access to and egress from the intracrystalline free space by virtue of having an effective pore size intermediate between the small pore Linde A and the large pore Linde X. The pore windows of the ZSM-12 structure are elliptical with a major diameter of about 6.1 angstroms and a minor diameter of 5.7 angstroms.

The silica to alumina mole ratio of ZSM-12 may be determined by conventional analysis. This ratio is meant to represent, as closely as possible, the ratio in the rigid anionic framework of the ZSM-12 zeolite crystal and to exclude aluminum in the binder or in cationic or other form within the channels. Although zeolites with a silica to alumina mole ratio of at least 12 are useful, it is preferred in some instances to use ZSM-12 zeolites having substantially higher silica/alumina ratios, e.g. 90:1 and above.

Members of this particular class of zeolites, after activation, acquire an intracrystalline sorption capacity for normal hexane which is greater than that for water, i.e., they exhibit "hydrophobic" properties. This hydrophobic character can be used to advantage in some applications.

Zeolites of the particular class useful herein have an effective pore size such as to freely sorb normal hexane. In addition, their structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Rather than attempt to judge from crystal structure whether or not a zeolite possesses the necessary constrained access to molecules of larger cross-section than normal paraffins, a simple determination of the "Constraint Index" may be made in accordance with the technique disclosed in U.S. Pat. No. 4,387,259, incorporated herein by reference.

The "Constraint Index" which is calculated as follows:

$$\text{Constraint Index} = \frac{\log_{10}(\text{fraction of hexane remaining})}{\log_{10}(\text{fraction of 3-methylpentane remaining})}$$

approximates the ratio of the cracking rate constants for the two hydrocarbons. Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| ZSM-50 | 2.1 |
| TMA Offretite | 3.7 |
| Clinoptilolite | 3.4 |
| Beta | 0.6 to 2.0 |
| H—Zeolon (mordenite) | 0.4 |
| REY | 0.4 |
| Amorphous Silica-Alumina | 0.6 |
| Erionite | 38 |

In the ZSM-12 zeolite, the original cations can be subsequently replaced, at least in part, by calcination and/or ion exchange with another cation or impregnation with another cation or metal. For the purposes of the present invention, ZSM-12 is ion-exchanged with cation or impregnated with copper cation. U.S. Pat. No. 4,019,880 a describes a suitable copper-loading method.

As has heretofore been stated, the novel process of this invention is adapted for cyclodimerization of 1,3-butadiene, in the presence of a copper-containing ZSM-12 zeolite catalyst as previously described. The cyclodimerization of 1,3-butadiene proceeds as follows to yield 4-vinylcyclohexene-1:

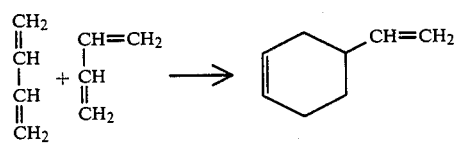

Other alkadienes which can be cyclodimerized are illustrated by isoprene, chloroprene, 1,3-pentadiene, cyclopentadiene, and the like. The cyclodimerization also can be effected between different conjugated dienes, and between dienes and monoalkenes, and the like. For example, maleic anhydride can be reacted with cyclopentadiene. Conjugated alkadienes can also be co-cyclized with alkynes such as dimethylacetylene.

An important advantage of the invention process is that high conversions are obtained with intermediate pore size zeolites as opposed to the prior art methods of carrying out said reaction with large pore size low acidity zeolites in the manner previously described. The process of the invention can be conducted in several ways, including continuous process in the gas phase or in the liquid phase, or as a batch process. The 1,3-butadiene dimerization, for example, can be accomplished at temperatures in the range of about 20° C. (room temperature) to temperatures as high as 400° C. or 500° C. However, the preferred temperature range is about 150° C. to 300° C. The reaction preferably is conducted at a pressure of about 50-1000 psi, and the product is recovered from the reaction mixture by standard procedures such as fractional distillation or the like.

It was unexpected that a Diels-Alder reaction such as the cyclodimerization of 1,3-butadiene to 4-vinylcyclohexene-1 could be significantly catalyzed by an intermediate pore size zeolite.

It is an important aspect of the invention process that the cyclization product resulting from the catalyzed Diels-Alder reaction must have sufficiently small molecular dimensions to permit the diffusion of said product out of the pore structure of the copper-containing ZSM-12 zeolite catalyst.

The following examples are further illustrative of the invention process.

EXAMPLES 1-2

Copper-exchanged ZSM-5 and ZSM-12 catalysts were prepared as follows:

16 g of $NH_4ZSM-5$ were added to a clear, filtered solution of 60 g of $CuCl_2 \cdot 2H_2O$ in 400 ml of $H_2O$. The mixture was stirred at about 21° for four hours. The exchanged zeolite was thereafter filtered from the solution and washed with water.

1.5 g of $NH_4ZSM-12$ were added to a clear filtered solution of 10 g of $Cu(OAc^-)_2$ and 150 ml of $H_2$. The mixture was stirred at about 21° for four hours. The exchanged zeolite was thereafter filtered from the solution and washed with water.

The cyclodimerization of 1,3butadiene was conducted in a downflow glass reactor packed with 0.5 g of catalyst. The 1,3-butadiene flow was adjusted to about 10 cc/min. and the temperature raised to about 200° to 250° C. The reaction effluent was sampled with an in-line gas chromatograph and the liquid product was collected for analysis by gas chromatograph mass spectroscopy. The results obtained were as follows:

| Catalysis Of 1,3-Butadiene Cyclodimerization | | | |
|---|---|---|---|
| Example | Catalyst | $SiO_2/Al_2O_3$ | % Conversion |
| 1 | CuZSM-5 | 70 | 0.3 |
| 2 | CuZSM-12 | 95 | 20 |

The above table illustrates the novel process of this invention in that the copper form of the intermediate pore size zeolite ZSM-12 in Example 2 unexpectedly converts 20 wt. % 1,3-Butadiene while the copper form of the intermediate pore size zeolite ZSM-5 converts only about 0.3 wt. % of the alkadiene.

What is claimed is:

1. A process for cyclodimerization of a conjugated alkadiene which comprises contacting a conjugated alkadiene-containing feedstock with a catalyst comprising copper-containing crystalline silicate having the structure of ZSM-12 at between about 20°-500° C., to yield cyclodimerized product.

2. The process of claim 1 wherein said contacting occurs at between about 150°-300° C.

3. The process in accordance with claim 1 wherein the conjugated alkadiene is 1,3-butadiene, and the cyclodimerized product is 1-vinylcyclohexene-1.

4. The process in accordance with claim 1 wherein the conjugated alkadiene is selected from the group consisting of isoprene, 1,3-pentadiene and cyclopentadiene.

* * * * *

UNITED STATES PATENT AND TRADEMARK OFFICE
CERTIFICATE OF CORRECTION

PATENT NO.   :   4,665,247

DATED        :   May 12, 1987

INVENTOR(S)  :   Ralph M. Dessau

It is certified that error appears in the above-identified patent and that said Letters Patent is hereby corrected as shown below:

Column 1, line 41, "3,832,149" should read --3,832,449--.

Column 3, line 11, "opposcd" should read --opposed--.

Column 3, line 45, after "21°" insert --C--.

Column 4, line 5, after "21°" insert --C--.

Signed and Sealed this

Tenth Day of November, 1987

Attest:

DONALD J. QUIGG

Attesting Officer

Commissioner of Patents and Trademarks